(12) United States Patent
Bruch et al.

(10) Patent No.: US 7,391,557 B1
(45) Date of Patent: Jun. 24, 2008

(54) MOBILE TERAWATT FEMTOSECOND LASER SYSTEM (MTFLS) FOR LONG RANGE SPECTRAL SENSING AND IDENTIFICATION OF BIOAEROSOLS AND CHEMICAL AGENTS IN THE ATMOSPHERE

(75) Inventors: Reinhard Bruch, Reno, NV (US); Jutta Gietl, Reno, NV (US)

(73) Assignee: Applied Photonics Worldwide, Inc., Reno, NV (US)

( * ) Notice: Subject to any disclaimer, the term of this patent is extended or adjusted under 35 U.S.C. 154(b) by 489 days.

(21) Appl. No.: 10/809,932

(22) Filed: Mar. 26, 2004

Related U.S. Application Data

(60) Provisional application No. 60/458,757, filed on Mar. 28, 2003.

(51) Int. Cl.
*H01S 3/00* (2006.01)
*G01B 9/02* (2006.01)
(52) U.S. Cl. .................. 359/333; 356/450; 356/451
(58) Field of Classification Search ............... 356/450, 356/491, 451, 18; 372/25; 359/333
See application file for complete search history.

(56) References Cited

U.S. PATENT DOCUMENTS

| | | | |
|---|---|---|---|
| 5,175,664 A | | 12/1992 | Diels et al. |
| 5,235,606 A | * | 8/1993 | Mourou et al. ............... 372/25 |
| 5,541,947 A | * | 7/1996 | Mourou et al. ............... 372/25 |
| 5,726,855 A | | 3/1998 | Mourou et al. |
| 6,208,458 B1 | * | 3/2001 | Galvanauskas et al. ...... 359/345 |
| RE37,585 E | * | 3/2002 | Mourou et al. .......... 219/121.69 |
| 6,760,356 B2 | * | 7/2004 | Erbert et al. .................. 372/93 |
| 6,930,779 B2 | * | 8/2005 | McGrew ..................... 356/450 |
| 7,012,698 B2 | * | 3/2006 | Patzwald et al. ............. 356/504 |
| 7,184,143 B2 | * | 2/2007 | Chin ........................... 356/318 |

OTHER PUBLICATIONS

U.S. Appl. No. 60/412,535, filed Sep. 20, 2002, Bruch et al.
A. Braun, et al., *Self-channeling of high-peak-power femtosecond laser pulses in air*, Optics Letters, vol. 20, 73-73 (1995).
Catherine Favre, et al., *White-Light Nanosource and Directional Emission*, Physical Review Letters, vol. 89, 035002-1-035002-4 (2000).

(Continued)

*Primary Examiner*—Mark Hellner
(74) *Attorney, Agent, or Firm*—Mintz, Levin, Cohn, Ferris, Glovsky and Popeo, P.C.

(57) ABSTRACT

The present invention relates to a system for detection and identification of airborne biological, chemical and/or nuclear threats such as toxins, spores, bacteria, and viruses in real time at distances from a few meters to several kilometers. Compact femtosecond terawatt laser technology is combined with spectroscopic and mathematical methods for spectral sensing of airborne warfare agents such as bio-aerosols. Trigger sensors and standoff devices based on mobile terawatt femtosecond laser systems are provided that may be placed at strategic monitoring locations. Furthermore, the invention relates to the propagation of airborne ultra-short, ultra-intense laser pulses giving rise to plasma channels (filamentation) producing white light supercontinuum ranging from the ultraviolet (UV), visible (VIS), near infra-red (NE) and middle infra-red (MIR). According to this invention, the supercontinuum can be directly produced in a particle cloud and hence is uniquely suitable for multi-spectral long-range atmospheric agent and radioactive isotope detection.

24 Claims, 8 Drawing Sheets

OTHER PUBLICATIONS

D.A. Ligon, et al., *Simulation of the Passive Infrared Spectral Signatures of Bioaerosol and Natural Fog Clouds Immersed in the Background Atmosphere*, Optics Express, vol. 10, 909-919 (2002).

Dieter Naumann, et al., *What Can Infrared Spectroscopy Tell Us About the Structure and Composition of Intact Bacterial Cells?*, Infrared Spectroscopy of Biomolecules, ed. by H.H. Mantsch and D. Chapman, Wiley-Liss, New York (1996).

*Differential Optical Absorption Spectroscopy (DOAS)*, U. Platt, Air Monitoring by Spectroscopic Techniques (Chemical Analysis, vol. 127), M.W. Sigrist (ed.), Wiley-Interscience (1994).

G.S. Sarkisov, et al., *Self-focusing, Channel Formation, and High-Energy Ion Generation in Interaction of an Intense Short Laser Pulse with a HE Jet*, Physical Review E, vol. 59, 7042-7054 (1999).

H. Wille, et al., *Teramobile: A Mobile Femtosecond-Terawatt Laser and Detection System*, European Physical Journal Applied Physics, vol. 20, 183-190 (2000).

J. Kasparian, et al., *Infrared Extension of the Supercontinuum Generated by Femtosecond Terawatt Laser Pulses propagating in the Atmosphere*, Optics Letters, vol. 25., 1397-1399 (2000).

J. Kasparian, et al., *The Critical Laser Intensity of Self-guided Light Filaments in Air*, Applied Physics B, vol. 71, 877-879 (2000).

Jean-Claude Diels, et al., *Ultrashort Laser Pulse Phenomena*, Optics and Photonics, Academy Press, San Diego (1996).

M.O. Scully, *FAST CARS: Engineering a laser spectroscopic technique for Rapid Identification of Bacterial Spores*, Proceedings of the National Academy of Sciences, vol. 99, 10994-1101 (2002).

P. Rairoux, et al., *Remote Sensing of the Atmosphere Using Ultrashort Laser Pulses*, Applied Physics B, vol. 71, 573-580 (2000).

P.B. Corkum, et al., *Supercontinuum Generation in Gases*, Physical Review Letters, vol. 57, 2268-2271 (1986).

Senator Bill Frist, M.D., *When Every Moment Counts: What you Need to Know About Bioterrorism From the Senate's Only Doctor*, Roman and Littlefield Publishers, Lanbam (2002).

Steve C. Hill, et al, *Enhanced Backward-Directed Multiphoton-Excited Fluorescence from Dielectric Microcavities*, Physical Review Letters, vol. 85, 54-57 (2000).

\* cited by examiner

31
UV-VIS Flourescence

27
fs-TW Laser
800nm

28
Two-colored Filament
800nm / 266.7nm

Aerosol 29

**IR Channel
30**

**Scattering Channels
32**

Baccillius Subtilis Extinction Aerosol Spectrum

$\sigma = 3.9 \times 10^{-7} / \lambda^{2.95}$ (Mie scattering background)

Baccillius Subtilis Absorption Aerosol Spectrum

Fig. 4

MOBILE TERAWATT FEMTOSECOND LASER SYSTEM (MTFLS) FOR LONG RANGE SPECTRAL SENSING AND IDENTIFICATION OF BIOAEROSOLS AND CHEMICAL AGENTS IN THE ATMOSPHERE

This patent application claims the benefit of U.S. Patent Application Ser. No. 60/458,757, filed Mar. 28, 2003 which is hereby fully incorporated by reference.

FIELD OF THE INVENTION

The present invention is related to detection and identification of airborne biological and chemical threats in real time at distances from a few meters to several kilometers. Advanced compact femtosecond terawatt laser technology is combined with state-of-the-art spectroscopic and computational methods. These methods are implemented in a unique mobile standoff detection system.

BACKGROUND OF THE INVENTION

U.S. Pat. No. 5,175,664 to Diels et al. describes a method and arrangement for discharge of lightning using ultra-short laser pulses. This proposed method enables discharges of electricity transmitted via conductive ionized channels produced by one or more first laser pulses of wavelengths essentially within the ultraviolet (UV) range. The preferred wavelength of operation is about 248 nm and the pulse duration of the laser is of the order of 100 fs. In accordance with this invention, lightning is triggered by creating an ionized channel by one or more femtosecond UV pulses and simultaneously sending one or more laser pulses of longer wavelength and duration through the same path. In this way the conductivity of the laser induced channel can be maintained long enough for discharges and lightning to occur. However, this patent does not address applications associated with atmospheric spectral sensing of atmospheric gases, pollutants and biological agents using femtosecond terawatt laser generated filaments as light sources.

One other related reference is U.S. Pat. No. 5,726,855 to Mourou et al., entitled "Apparatus and Method for Enabling the Creation of Multiple Extended Conduction Paths in the Atmosphere" which claims an apparatus and method for the creation of multiple extended conduction paths in the atmosphere using high peak-power ultra-short laser pulses. Furthermore, the same group published addressing long range self-channeling of intense femtosecond pulses in air in 1994 by Mourou and co-workers. The focus of their patent is centered on an apparatus for controlling the discharge of lightning strikes and grounding means using a grounding tower. Also no claims are made regarding spectroscopic optical sensing and identification of bio-agents using multiple extended conduction paths in the atmosphere.

It will therefore be appreciated that there remains a need for an improved system and technique for determining whether certain molecules, such as bioaerosols and chemical agents, may be found within a sample.

SUMMARY OF THE INVENTION

Early warning of biological attack and plume prediction for biological aerosols require the capability to detect bio-agents over large distances. Thus, the present invention relates to a complex bio-agent sensing system based on the principle of using femtosecond terawatt lasers, preferentially titanium sapphire laser systems in conjunction with chirp-pulse amplification and compression. The propagation of such ultra-short laser pulses gives rise to strongly non-linear optical processes in the atmosphere, leading to filamentation of the laser pulse at a specific distance. Conducting plasma channel produce a white-light supercontinuum spanning the ultraviolet (UV), visible (VIS) and infrared (IR). Wavelength region. This novel atmospheric lamp can be used for spectroscopic analysis of bio-agents by means of a Lidar (Light Detection and Ranging) system. The supercontinuum can be generated directly in a particle cloud and hence is suitable for multi-spectral long-range detection and identification of bio-aerosols as well as chemical pollutants and radioactive isotopes. According to the invention, compact femtosecond terawatt laser technology is applied in combination of state-of-the-art spectroscopic and computational methods for spectral sensing of bio-aerosols with molecular specificity.

The current invention permits real time detection, discrimination, and identification of the full spectrum of threats including; toxins, spores, bacteria and virus. The sensing range spans up to 10,000 meters and can be applied to airborne versions together with stand alone trigger devices at strategically vital locations on sea, air or land.

This invention presents a promising new trigger sensor and a standoff detection system that can identify airborne biological, chemical, and nuclear agents within a few seconds at distances from a few meters to several kilometers. The biological agent-sensing device is based on the principle of remote differential time resolved monitoring of the atmosphere using ultrashort terawatt laser pulses. According to this invention, concept of advanced compact femtosecond Terawatt (fs-TW) laser technology is combined with state-of-the-art spectroscopic and computational methods. The stand off sensing technology permits real time detection, discrimination, and identification of the full spectrum of threats including; toxins, spores, bacteria and virus. The sensing range spans up to 10,000 meters and can be applied to airborne versions together with stand alone devices at strategically vital locations on sea, air or land. This system would reduce the probability of false alarm and time for detection by more than one order of magnitude. The minimum anticipated range would be of the order of 5-10 spores per liter of air.

In one embodiment, the invention is provided in a system for determining the constituents of a sample, the system comprising, a femtosecond terawatt laser radiation source configured to emit laser radiation through a sample, an optical unit configured to receive light backscattered from the sample, and a detection and analysis unit coupled to the optical unit for analyzing a spectral signature of the sample. The system may also an optical fiber cable coupling the optical unit to the detection and analysis unit.

In some variations, the detection and analysis unit comprises an integrated diagnostic unit having one or more infrared and UV/VIS spectrometers with gated detection capability, two photo-multipliers attached to an air transient digitizer, and a data acquisition control unit. In addition, or in the alternative, the detection and analysis unit may further comprise a real-time computing system for identification and discrimination of at least one of the group comprising aerosols, airborne bacteria, viruses, toxins, dust particles, pollen, water droplets, gaseous agents, and pollutants.

The femtosecond terawatt laser radiation source may be amplified by a variety of techniques such as chirped pulse amplification. It may also be, in some examples, a laser such as a Ti:Sapphire laser that is configured to emit energy of approximately 300 mJ per pulse. The femtosecond terawatt laser radiation source may have a pulse power of about approximately 3 and 4 TW with a pulse duration approximately of the order of 80 to 100 fs and a repetition rate of approximately 10 Hz. It may emit light within a spectral range approximately centered at 800 nm or 267 nm with a spectral width of approximately 20 nm. In addition, the femtosecond laser radiation source may emits laser pulses at a center wavelength of approximately 800 nm and spectral width of 20 nm to create plasma filaments as well as at a wavelength of approximately 267 nm.

The detection and analysis unit may configured to detect airborne biological, chemical agents and water droplets by at least one technique chosen from the group comprising: differential absorption, Raman Raleigh and Mie scattering, fluorescence, fluorescence LIDAR measurements, ground-based LIDAR measurements, air-based LIDAR measurements, and Raman LIDAR measurements. The detection and analysis unit may also be configured to provided 3D maps or other representations of detected molecules to further assist with their identification.

In another variation, the invention is embodied in a method for determining the constituents within a sample, the method comprising the steps of providing a femtosecond terawatt laser radiation source configured to emit laser radiation through a sample, capturing light backscattered from the sample, and analyzing a spectral signature of the sample to determine its constituents.

The analyzing step may determine whether the constituents include least one of the group comprising: aerosols, airborne bacteria, viruses, toxins, dust particles, pollen, water droplets, gaseous agents, and pollutants.

The method may also include the step of amplifying the femtosecond terawatt laser radiation source using chirped pulse amplification.

In some variations, the femtosecond terawatt laser radiation source is a laser such as a Ti:Sapphire laser configured to emit energy of approximately 300 mJ per pulse. The method may also include the step of pulsing the femtosecond terawatt laser radiation source at a power of about approximately 3 and 4 TW with a pulse duration approximately of the order of 80 to 100 fs and a repetition rate of approximately 10 Hz. The femtosecond terawatt laser radiation source may emit light within a spectral range approximately centered at 800 nm or 267 nm with a spectral width of approximately 20 nm.

Optionally, the femtosecond laser radiation source may emit laser pulses at a center wavelength of approximately 800 nm and spectral width of 20 nm to create plasma filaments as well as at a wavelength of approximately 267 nm.

Depending on the desired implementation, the analyzing step may use at least one technique chosen from the group comprising: differential absorption, Raman Raleigh and Mie scattering, fluorescence, fluorescence LIDAR measurements, ground-based LIDAR measurements, air-based LIDAR measurements, and Raman LIDAR measurements for determining which constituents are present within a sample.

The method may also include the step of generating a 3D map or image of the detected constituents. The constituents may be determined, in part, by the step of comparing at least one of detected vibrational bands, detected Raman spectra, and fluorescence spectra, with previously measured spectral data to identify the constituents within the sample.

A mobile femtosecond terawatt LIDAR system and/or trigger sensor for long-range analysis with high temporal and spatial resolution and spectroscopic identification of airborne biological and chemical agents is also provided. Such a system includes a femtosecond terawatt laser radiation source based on the principle of chirped pulse amplification (CPA), preferably a Ti:Sapphire laser system having an energy of approximately 300 mJ per pulse resulting in a pulse power of about 3 and 4 TW with a pulse duration of the order of 80 to 100 fs and a repetition rate of 10 Hz. The laser source emits light in the spectral range of approximately 800 nm with a spectral width of approximately 20 nm or laser pulses with a wavelength of about 267 nm corresponding to third harmonic generation (SHG). The system also includes an optical system coupled to the laser radiation source including sending and receiving telescopes, an integrated diagnostic system embracing infrared and UV/VIS spectrometers with gated detection capability, two photo-multipliers attached to air transient digitizer and data acquisition control system, and a real-time computing system (using techniques such as neural networks, fuzzy logic and other advanced computational techniques) for identification and discrimination of at least one of the group comprising: aerosols, airborne bacteria, viruses, toxins, dust particles, pollen, water droplets, gaseous agents, and pollutants.

The system may provide for remote monitoring of the atmosphere using ultra-short terawatt laser pulses giving rise to strongly nonlinear optical processes in the air thus generating plasma channel type of filaments encompassing: NIR femtosecond laser pulses at a center wavelength of approximately 800 nm and spectral width of 20 nm creating plasma filaments caused by self-channeling/guiding effects and producing a supercontinuum atmospheric light source ranging for optical sensing applications from the UV to the MIR and UV femtosecond laser pulses operating at a wavelength of approximately 267 nm corresponding to the SHG creating no new wavelengths but propagating with much lower losses up to several km through the plasma channel when compared to the NIR laser pulses.

Femtosecond laser pulses centered at 800 nm may be used to produce a broadband supercontinuum light source in the atmosphere for sensing of airborne biological, chemical agents and water droplets by means of differential absorption and/or fluorescence LIDAR measurements. In addition or in the alternative, femtosecond laser pulses centered at 267 nm are used for sensing of airborne biological, chemical agents and water droplets by means of fluorescence and/or Raman LIDAR measurements. Femtosecond laser pulses centered at 800 nm and 267 nm may be used for sensing of airborne biological, chemical agents and water droplets by means of ground based and air based LIDAR measurements. Femtosecond laser pulses centered at 800 nm and 267 nm may be used for sensing of airborne biological, chemical agents and water droplets by means of ground based and air based LIDAR measurements.

The system may also compare the most significant vibrational bands (fingerprint regions) of these bio-aerosols, chemical agents and water droplets with existing laboratory spectral data to rapidly detect and identify such agents for multi-spectral long-range atmospheric agent detection of clouds and plumes. In other variations, the system compares the most significant Raman and fluorescence spectra (fingerprint regions) of bio-aerosols, chemical agents and water droplets with existing laboratory spectral data to rapidly detect and identify such agents for multi-spectral long-range atmospheric agent detection of clouds and plumes.

One aspect of the invention is that it provides high range resolution over long distances to record the signal of the backscattered light due to Raleigh and Mie scattering from gaseous molecules, bio-aerosols and water droplets in the clouds and plumes. It combines the advantages of the remote sensing techniques and their broadband spectral resolution, with 3D mapping capability. This permits the simultaneous measurement of several bio-aerosol compounds, even with over Furthermore, the invention provides sophisticated differential absorption, fluorescence, Raman Raleigh and Mie scattering, multi-channel, multi-wavelength, multi-spectral LIDAR system for ground based and air based monitoring of bio-aerosols and chemical agents in real time with high accuracy and reduced false alarms for long range detection from about a few meters to 10 km.

The invention may also be embodied in a complex trigger sensor/standoff system with substantially improved performance requirements for probability of detection, probability of false alarm, time for detection and threat level when compared to existing technologies. The invention may be used in a variety of settings including water treatment plants, environmentally sensitive areas e.g. subways, airports, government buildings, military facilities, industrial complexes and cities as mobile trigger points, area sensors and standoff systems.

BRIEF DESCRIPTION OF THE DRAWINGS

FIG. 1 is a diagrammatic view of the femtosecond LIDAR system for long-range detection of bio-aerosols;

FIG. 2 is a schematic view of different spectroscopic excitation and de-excitation channels in the infrared and ultraviolet including scattering processes;

FIG. 3 is a bacillus subtilis extinction aerosol spectrum in the MIR and far IR region;

FIG. 4 is a bacillus subtilis absorption aerosol spectrum in the MIR region;

DETAILED DESCRIPTION OF THE INVENTION

Figure 1:
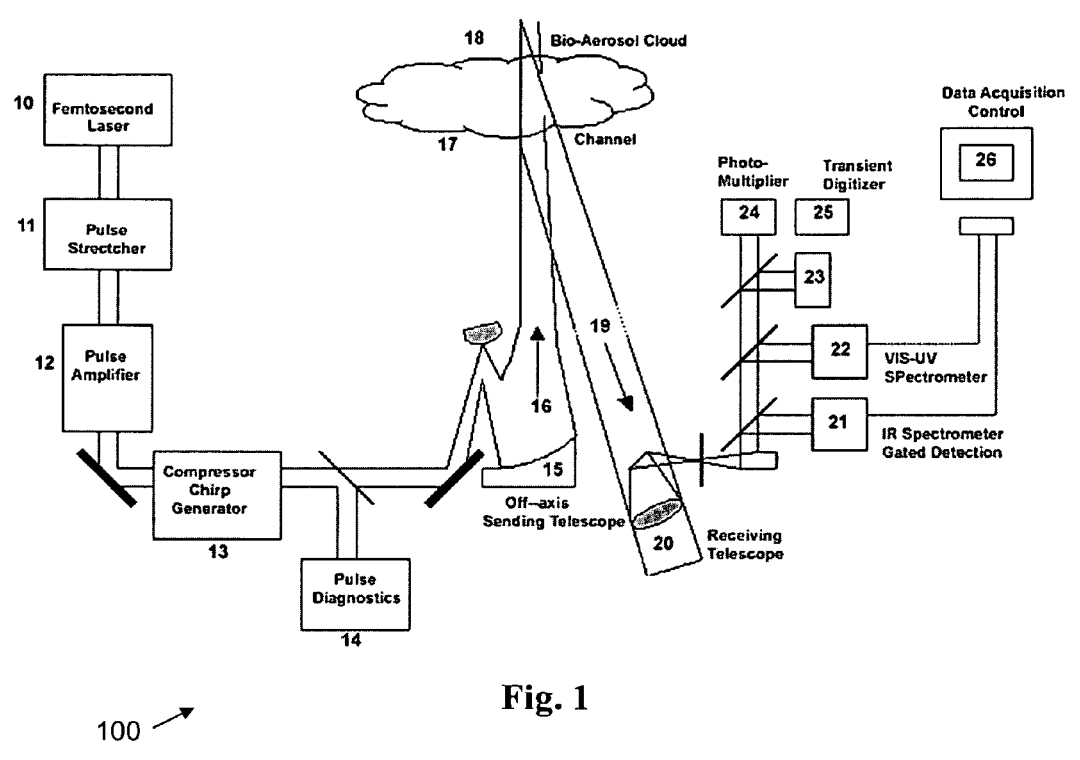
Figure 5:
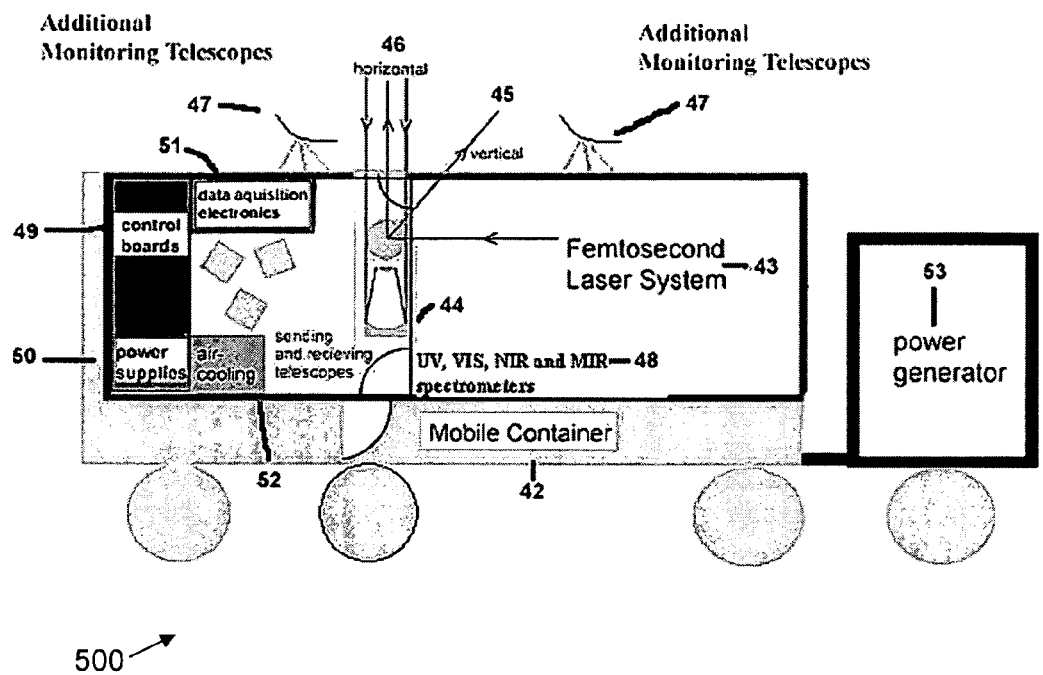
FIG. 5 is an example of a mobile ground based standoff LIDAR system useful for understanding and implementing the invention.

According to this invention, an fs-TW laser system is comprised of a femtosecond laser (10), pulse stretcher (11), pulse amplifier (12) and chirp generator (13). The final pulse duration is approximately 80 to 100 fs and the energy is of the order 300 mJ per pulse resulting in a pulse power between approximately 3 and 3.5 TW. The pulse shape is analyzed by a pulse diagnostic system (14) and then directed to an off-axis telescope (15). The slightly focused laser beam (16) then creates a channel (filament) in the atmosphere (17) and the emitted light from the filament interacts with the bio-aerosol cloud (18). The backscattered light (19) is collected by means of a receiving telescope (20) and then analyzed by different types of spectrometers (21 and 22) and photo-multipliers (23 and 24), where the IR spectrometer (21) measures the differential absorption in the bio-cloud and the VIS/UV spectrometer (22), the absorption and/or fluorescence of the cloud. As can be seen in FIG. 1, the photo-multiplier signals (23 24) are fed to transient digitizer (25). Finally the data acquisition and control system (26) receives signals from the different detection devices.

The diagrammatic view (100) of FIG. 1 represents a standoff laser system with a complex integrated detection setup that can be used as a biological chemical and environmental agent monitoring arrangement. This system is based on the principle of remote sensing and monitoring of the atmosphere using ultra short terawatt laser pulses. The propagation of these laser pulses gives rise to strong nonlinear optical processes in air maybe producing filamentation type of conducting plasma channels where in-turn a white-light supercontinuum (16) is created. This supercontinuum can be located directly in a bio-pathogen cloud (24), and its wavelength extends from the ultraviolet (UV) to the infrared (IR).

The present invention relates to currently available fs-TW laser systems based on the chirped pulse amplification (CPA) technique using Titanium: Sapphire as the active laser crystal. These lasers provide a broadband spectral distribution of light centered at a wavelength of about 800 nm. The aim of the invention is detecting and specifying bio-aerosols using different approaches such as: (a) detection through differential absorption and UV fluorescence and (b) detection through modification of the optical characteristics of the plasma channels generated in air at different locations. In either case, light emitted in the near-backward region from an aerosol source is spectroscopically and temporally analyzed in the vicinity of the laser beam propagation. The receiver systems are capable of yielding spectra from the UV through the VIS into the MIR region (from about 270 to 5500 nm). Field test experiments will be used for different types of aerosols including water droplets, inorganic atmospheric aerosol (ammonium sulphate), common non-biological organic atmospheric aerosol (i.e., organic carbon), common biological atmospheric aerosol (e.g., pollen), airborne bacteria, viruses, toxins, dust particles, pollen, water droplets, diesel dust, gaseous agents and other biological aerosol serving as surrogate.

An object of this invention is complex plume prediction schemes and early warning systems for biological attacks. As shown in schematic (200) of FIG. 2, an fs-TW laser (27) creates a two-colored filament (28) at a specific location in the atmosphere with the wavelength of approximately 800 nm, where the laser pulses interact with specific aerosols at different distances (29). As indicated in FIG. 2 the third harmonic generation (THG) component of the laser propagating inside the filament channel (28) can also be used as a new diagnostic technique. Different strategies are used to understand and interpret complex threats/attacks, namely due to simultaneously analysis of infrared differential absorption channels (30) and UV and visible channel fluorescence (31) produced by the long distance UV filaments created by 800 nm laser pulses. In addition, light scattering channels including Rayleigh, Mie and Raman scattering (32) will be observed to shed more light on the composition of different atmospheric constituents and background radiation.

The invention may also be used to study and identify micro-droplets, which represent a major part of atmospheric aerosols. They are attractive systems for the study of several nonlinear optical effects using fs-TW laser devices. They may act as lenses focusing the incident radiation onto some small regions inside the droplets and they also induce morphology dependent resonances, which can further enhance the laser intensity in the droplet. Hence, at the areas of high laser intensity the efficiency for nonlinear optical processes is strongly enhanced. The scattered wave and the internal intensity distribution depend on the refractive index of the droplet medium and on the size parameter, which is the ratio of the droplet circumference to the wavelength of the incident light. When studying the interaction of femtosecond laser pulses with these micro-droplets, the large spectral bandwidth of the ultra short pulses has to be taken into account.

Figure 4:
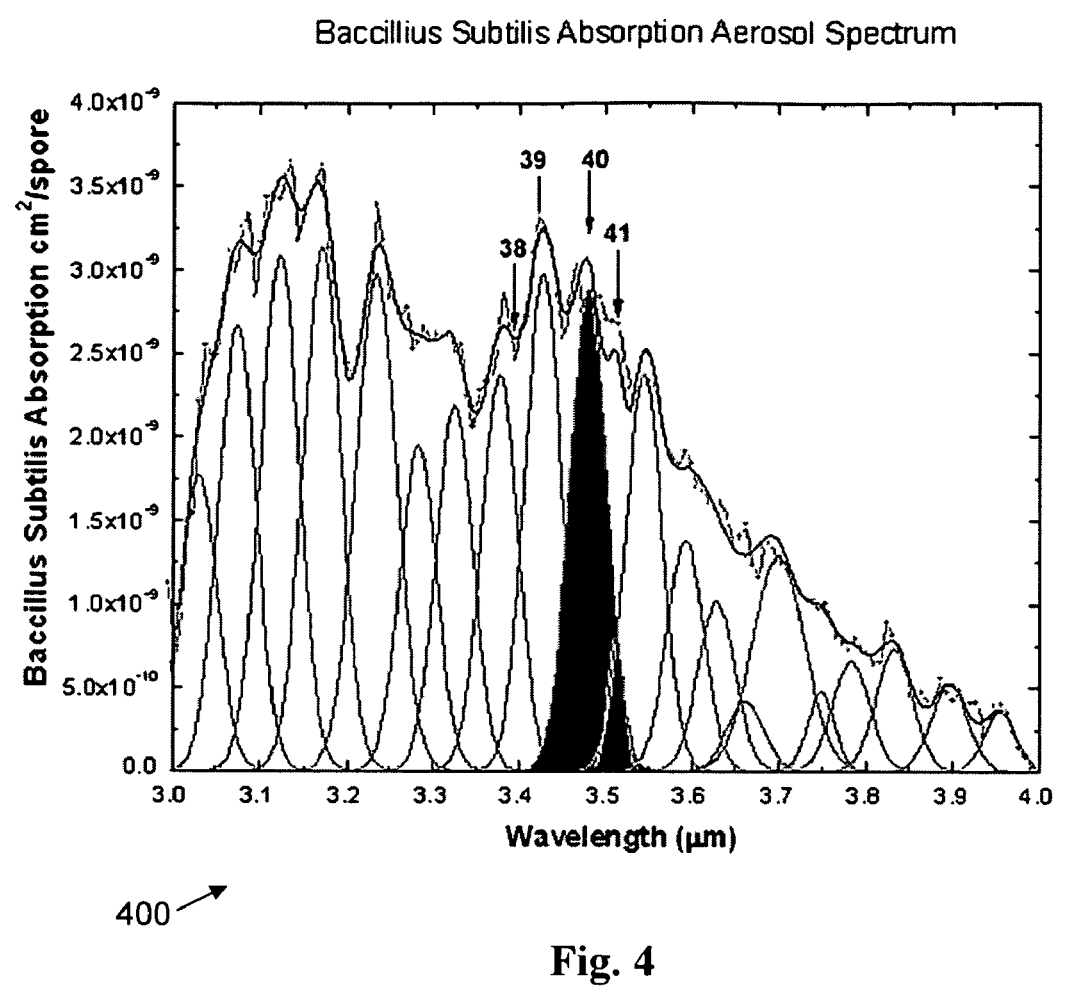

Another object of the present invention is to utilize vibrational spectroscopy of bio-agents. This approach includes extinction and scattering measurements to characterize the spectral fingerprints and change of conformation of the biological molecular systems. Therefore, the aim of this invention also is to compare the most significant vibrational bands (fingerprint regions) of such aerosols with existing laboratory spectral data to rapidly detect and identify such bio-agents. As described in FIG. 3, a characteristic IR spectrum (300) of aerosolized Bacillus subtilis var. niger (BG) spores in the 2.3-to 12-μm wavelength regions is shown. The bio-agent spectrum is composed of an absorption part superimposed on a Mie scattering background (33). The absorption spectrum exhibits specific spectral features at approximately 2.9-3.6 μm (34). The spectral peak at about 3.1 μm can be partially identified as the Amide A band. Moreover, the spectral features located in the 5.5 to 6.6 μm region are associated with the Amide I and Amide II bands (35). Additional important fingerprint regions occur in the range 6.6-8 μm (36). Moreover spectral features between 8-11 μm can be associated with Amide III band, phosphate groups and peptide backbone structures (37). In order to extract the most important spectral features (peak positions, widths, band structures, intensity ratios etc.), the noise associated with the spectral data has to be removed. Then an appropriate non-linear function due to Mie scattering will be used to fit the residual background following a peak fitting analysis. A typical resulting absorption spectrum (400) is displayed in FIG. 4 between 3-4 μm. Two different cases are considered here. In the first case, two substantially different atmospheric transmission channels (38 and 39) with similar absorption cross sections are examined. One can see here that there is a valley at the channel with lower atmospheric transmission (38) and a peak is achieved at the channel with higher atmospheric transmission (39). In the second case, constant atmospheric transmissions are considered although the absorption cross sections differ substantially. For example, channel (40) has a higher absorption cross section than channel (41) with a lower absorption cross-section. These patterns comprise the vibrational characters of the constituents such as DNA/RNA, proteins and cell wall components. Owing to the multitude of cellular components, broad and superimposed spectral bands are observed in the MIR range.

Another example (500) useful for understanding and implementing the invention is shown in FIG. 5. A schematic view of a ground based differential Mobile Multiple Wavelength Trigger Sensor system and/or Teramobile Lidar system is exhibited housed in a single mobile container (42). The setup consists of a tabletop terawatt femtosecond laser (43) and detection system with high spatial, spectral, and time resolution. The system is comprised of sending and receiving telescopes (44) with the vertical beam direction (45) and a horizontal beam direction (46). The mobile container also has additional monitoring telescopes for trigger sensors (47). The reflected and scattered light is fed to the different UV, VIS, NIR and MIR spectrometers and associated detection systems (48). For the amplification the system also houses control boards (49) and power supplies (50). For the data interpretational and computational purposes the system has an advanced data acquisition control system with several attached parallel computers (51) for real time data reduction, modeling and discrimination. The temperature conditions are controlled inside the mobile container with the help of air-cooling system (52). This system is driven with a power generator (53), which is placed separately outside the mobile container to minimize the evasive effect from vibrations.

Figure 6:
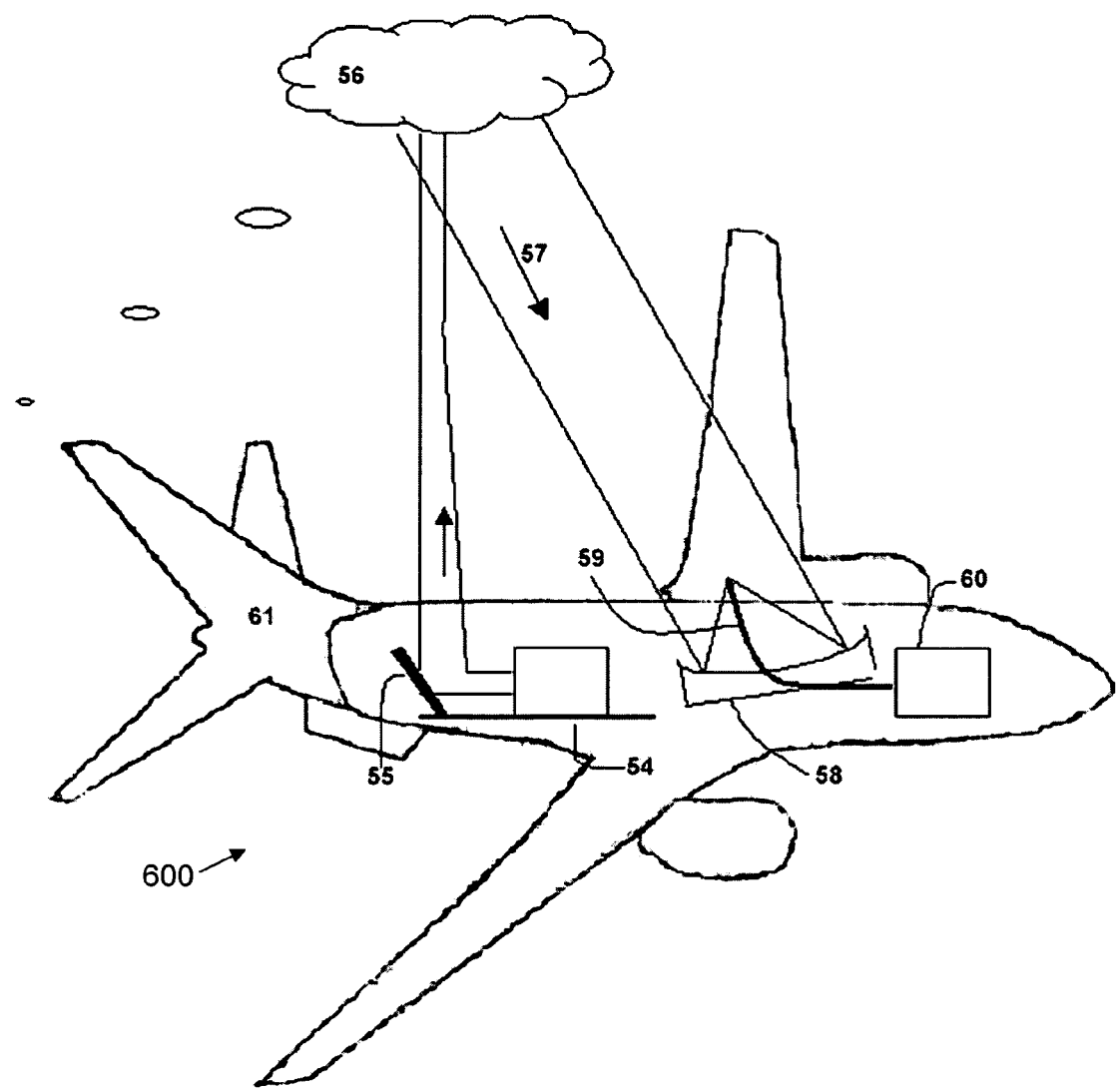
FIG. 6 is an example of a mobile air-based LIDAR system useful for understanding and implementing the invention.

In FIG. 6 an up looking airborne differential absorption femtosecond terawatt laser system (600) is shown. Such an airborne LIDAR system would be capable of a broad range of high priority measurements for use in an aircraft. This system could also be operated looking downwards from the aircraft compared with the system looking upwards from the ground. This improvement makes the LIDAR system an attractive airborne tool for both daytime and nighttime conditions. In the schematic diagram, a femtosecond terawatt laser (54) with adaptive optical elements (5S) direct the laser beam towards a bio-aerosol cloud (56) and backscattered light (57) is collected by a telescope mirror (58) and directed via an optical fiber cable (59) to time resolved spectrometer setup (60). The airplane (61) contains all the necessary power supplies, electronics, data acquisition control systems and parallel computers for real time modeling and discrimination.

The main advantage of this ultrafast ground based and air-based Lidar technique over other remote sensing methods (such as differential optical absorption spectroscopy, Fourier transform infrared spectroscopy and satellite based spectroscopy) is the high resolution over long distances, which is achieved by the use of short-pulse lasers and fast detection systems to record the signal of the backscattered light arising from gaseous molecules and aerosols femtosecond white-light Lidar combines the advantages of those remote sensing techniques and their broadband spectral resolution, with 3D mapping capability. This permits the simultaneous measurement of several bio-aerosol compounds, even with overlapping spectral signatures. Moreover, since the whole spectrum can be simultaneously acquired, the laser shot-to-shot fluctuations do yield much less systematic errors as commonly in the case for traditional Differential Absorption Lidar (DIAL) systems.

Such nonlinear effects induced by ultra short, high-power laser pulses in aerosols rely either on the micro cavity behavior of spherical micro-droplets, providing strong feedback for stimulated processes, or on the internal focusing of the incident light, providing high intensity hot spots where the efficiency for nonlinear optical processes is strongly enhanced.

High-intensity laser pulses can cause water droplets to emit white light. This technique can potentially be used to analyze the composition of clouds and shed more light on how clouds may contain bio-aerosols. This approach would also provide more information on cloud-aerosol interactions. The possibility of identifying the fingerprints of chemical components inside an individual water droplet may open up new ways to diagnose aerosol clouds and more localized sources.

The present invention also relates to pattern recognition procedures of the data consisting of four steps: i) cluster the feature vectors from a population of entities into classes via the robust fuzzy clustering algorithm, ii) compute a prototype for each class, iii) compute an inverse covariance matrix for each prototype and center a Gaussian fuzzy set membership function on it to construct a fuzzy classifier and place it on-line to receive incoming feature vectors. The 1-sigma (standard deviation) regions under each Gaussian are ellipsoidal in N dimensions (for N features), so a class may contain one or more ellipsoidal groups.

An alternative method related to this invention is to use the clustered signatures to train the powerful new radial basis functional link net, which learns faster and more efficiently than other types of neural networks (NN's). While there are NN's that learn, or self-organize themselves, they are relatively slow and do not learn robustly, so clustering should be done first and then supervised training should be done for the best results.

Figure 7:
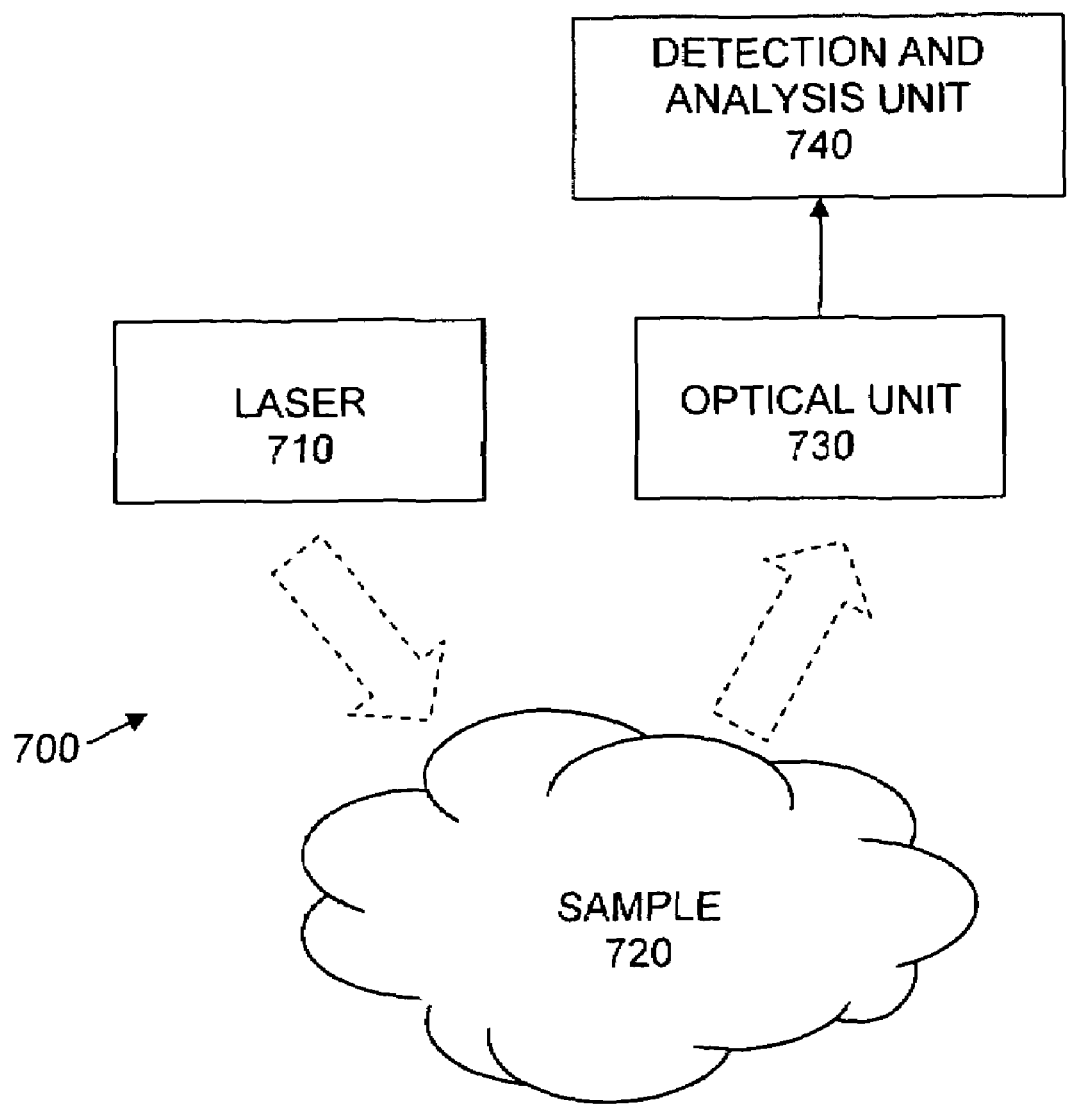
FIG. 7 is a schematic diagram illustrating a system embodiment of the invention.

FIG. 7 illustrates a schematic diagram of a system embodiment (700) of the current invention for determining the constituents of a sample (720). The system includes a femtosecond terawatt laser radiation source (710) configured to emit laser radiation through the sample (720), an optical unit (730) configured to receive light backscattered from the sample, and a detection and analysis unit (740) coupled to the optical unit for analyzing a spectral signature of the sample. This system may be used in connection with any of the above techniques and sub-systems to further enhance the detection and analysis of molecules or constituents of interest within the sample (720).

Figure 8:
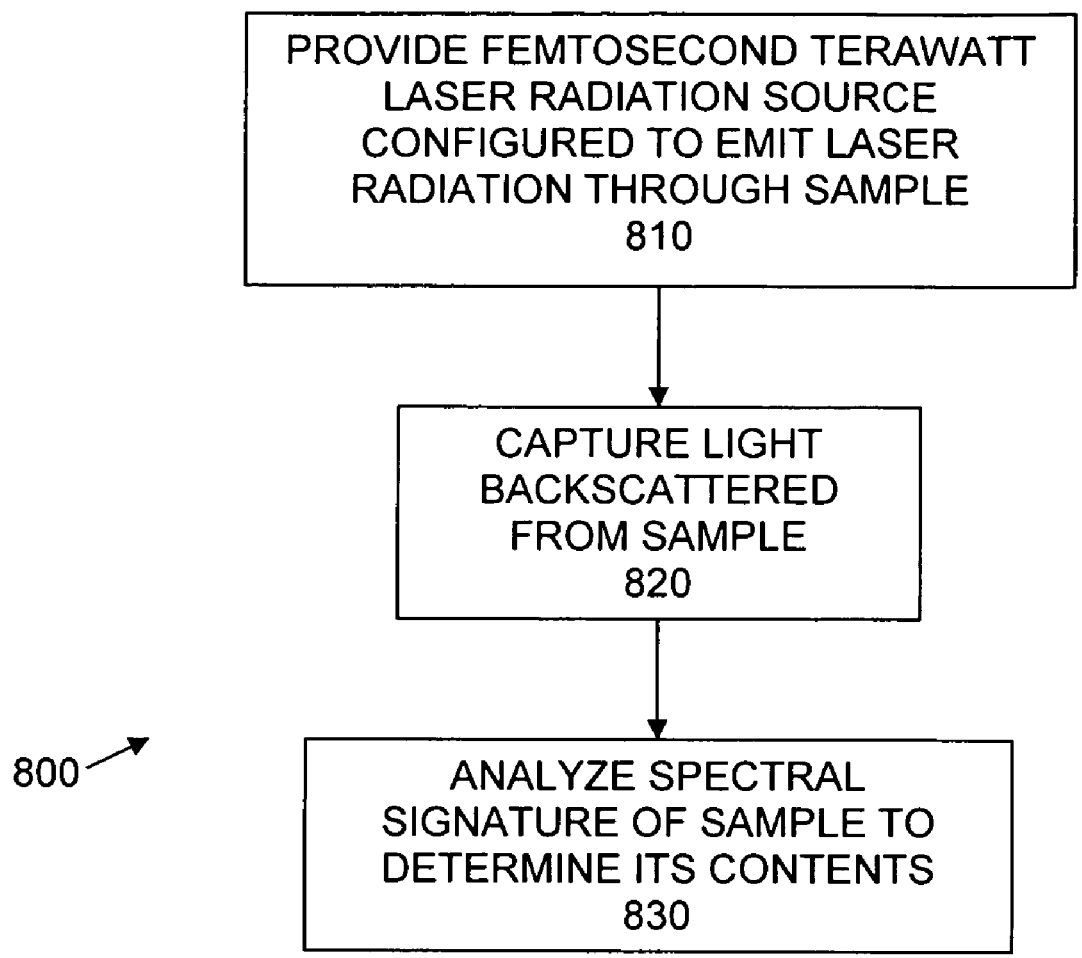
FIG. 8 is a process flow diagram illustrating a method embodiment of the invention.

Similarly, FIG. 8 illustrates a process flow diagram of a method embodiment (800) of the current invention useful for determining the constituents of a sample. At step (810), a femtosecond terawatt laser radiation source configured to emit laser radiation through sample is provided. Next, backscattered light from the sample is captured at step (820). The method ends, at step (830), with the analysis of the spectral signature of the sample as captured to determine its contents. As can be appreciated, the method may be implemented with any one of the above laser radiation systems as well as detection and analysis sub-systems.

The drawings and foregoing description are not intended to represent the only form of the invention in regard to the details of the construction and manner of operation. In fact, it will be evident to one skilled in the art that modifications and variations may be necessary without departing from the spirit and scope of the invention. Although specific terms have been employed, they are intended in generic and descriptive sense only and not for the purpose of limitation.

What is claimed is:

1. A system comprising:
   a femtosecond terawatt laser radiation source configured to emit laser radiation through a portion of the atmosphere;
   an optical unit configured to receive light backscattered from the portion of the atmosphere; and
   a detection and analysis unit coupled to said optical unit for analyzing a spectral signature of the portion of the atmosphere, the detection and analysis unit comprising an infrared spectrometer, a UV/VIS spectrometer, one or more photo-multipliers coupled to an air transient digitizer, and a data acquisition control unit coupled to the spectrometers.

2. The system of claim 1, further comprising an optical fiber cable coupling said optical unit to said detection and analysis unit.

3. The system of claim 1, wherein said detection and analysis unit further comprises a real-time computing system for identification and discrimination of at least one of the group comprising: aerosols, airborne bacteria, viruses, toxins, dust particles, pollen, water droplets, gaseous agents, and pollutants.

4. The system of claim 1, wherein said femtosecond terawatt laser radiation source is amplified by chirped pulse amplification.

5. The system of claim 1, wherein said femtosecond terawatt laser radiation source is a Ti:Sapphire laser configured to emit energy of approximately 300 mJ per pulse.

6. The system of claim 5, wherein said femtosecond terawatt laser radiation source has a pulse power of about approximately 3 and 4 TW with a pulse duration approximately of the order of 80 to 100 fs and a repetition rate of approximately 10 Hz.

7. The system of claim 1, wherein said femtosecond terawatt laser radiation source emits light within a spectral range approximately centered at 267 nm.

8. The system of claim 1, wherein said femtosecond laser radiation source emits laser pulses at a center wavelength of approximately 800 nm to create plasma filaments.

9. The system of claim 1, wherein the detection and analysis unit is configured to detect airborne biological, chemical agents and water droplets by at least one technique chosen from the group comprising: differential absorption, Raman LIDAR measurements and Raman, Raleigh and Mie scattering, and by at least one other technique chosen from the group comprising fluorescence, fluorescence LIDAR measurements, ground-based LIDAR measurements, and air-based LIDAR measurements.

10. The system according to claim 1, wherein the detection and analysis unit is configured to provide 3D maps of detected molecules.

11. A method comprising:
    providing a femtosecond terawatt laser radiation source configured to emit pulsed laser radiation at approximately 267 nm through a portion of the atmosphere to create plasma filaments;
    capturing light backscattered from the portion of the atmosphere; and
    analyzing a spectral signature of the portion of the atmosphere to determine its constituents;
    wherein an infrared spectrometer is utilized to measure a differential absorption in the portion of the atmosphere and a UV/VIS spectrometer is utilized for measuring absorption or fluorescence of the portion of the atmosphere.

12. The method of claim 11, wherein the analyzing step determines whether the constituents include least one of the group comprising: aerosols, airborne bacteria, viruses, toxins, dust particles, pollen, water droplets, gaseous agents, and pollutants.

13. The method of claim 11, further comprising the step of amplifying the femtosecond terawatt laser radiation source using chirped pulse amplification.

14. The method of claim 11, wherein the femtosecond terawatt laser radiation source is a Ti:Sapphire laser configured to emit energy of approximately 300 mJ per pulse.

15. The method of claim 11, further comprising the step of pulsing the femtosecond terawatt laser radiation source at a power of about approximately 3 and 4 Tw with a pulse duration approximately of the order of 80 to 100 fs and a repetition rate of approximately 10 Hz.

16. The method of claim 11, wherein the femtosecond terawatt laser radiation source is configured to emit light within a second spectral range approximately centered at 800 nm.

17. The method of claim 11, wherein the analyzing step uses at least one technique chosen from the group comprising: differential absorption, Raman, Raleigh and Mie scattering, fluorescence, fluorescence LIDAR measurements, ground-based LIDAR measurements, air-based LIDAR measurements, and Raman LIDAR measurements.

18. A method according to claim 11, wherein the detection and analysis unit is configured to provide 3D maps of detected molecules.

19. A method according to claim 11, further comprising the step of comparing at least one of detected vibrational bands, detected Raman spectra, and fluorescence spectra, with previously measured spectral data to identify the constituents within the sample.

20. A system comprising:
    means for providing a femtosecond terawatt laser radiation source configured to emit pulsed laser radiation at approximately 267 nm through a portion of the atmosphere to create a plasma filament;
    means for capturing light backscattered from the portion of the atmosphere comprising means for measuring a differential absorption in the portion of the atmosphere and means for measuring absorption or fluorescence of the portion of the atmosphere; and means for analyzing a spectral signature of the portion of the atmosphere to determine its constituents.

21. The system of claim 1, wherein said femtosecond laser radiation source emits laser pulses at a wavelength of approximately 267 nm.

22. A method comprising:
providing a femtosecond terawatt laser radiation source configured to emit laser radiation through a sample to generate a plasma channel;
capturing light backscattered from the sample by at least two photomultipliers;
analyzing at least one spectral signature of the sample to determine its constituents using at least two spectrometers coupled to at least two photomultipliers; and
characterizing the constituents of the sample based on the analyzed spectral signature;
wherein an infrared spectrometer is utilized to measure a differential absorption in the portion of the atmosphere and a UV/VIS spectrometer is utilized for measuring absorption or fluorescence of the portion of the atmosphere.

23. A method as in claim 21, wherein the radiation source emits light at approximately 267 nm.

24. The system of claim 1, wherein said femtosecond terawatt laser radiation source is configured to emit light within two spectral ranges, the first spectral range approximately centered at 267 nm and the second spectral range approximately centered at 800 nm.

* * * * *